US00PP08774P

United States Patent [19]

McRae

[11] Patent Number: Plant 8,774

[45] Date of Patent: Jun. 7, 1994

[54] LILY PLANT LILIUM CORAL FASHION

[75] Inventor: Judith F. McRae, Boring, Oreg.

[73] Assignee: Mt. Hood Lilies, Inc., Sandy, Oreg.

[21] Appl. No.: 100,706

[22] Filed: Jul. 30, 1993

[51] Int. Cl.[5] ..... A01H 5/00

[52] U.S. Cl. ..... Plt./87.4

[58] Field of Search ..... Plt. 87.4

*Primary Examiner*—David T. Fox

[57] ABSTRACT

A new variety of hybrid lily plant bearing large upfacing to outfacing flowers of excellent form and long persistence, both on the plant and as cut-flowers. The flowers of the new hybrid are particularly characterized by their large size and substance, their "open bell" form, their coral coloration, and their fragrance. This combination is completely new in the Longiflorum hybrid divisions of lilies suited to forcing and to mass commercial cultivation. The variety is highly resistant to fusarium disease and shows tolerance of virus. The bulbs may be precooled and forced for cut-flower production. The clone is vigorous and is a good grower and propagator.

1 Drawing Sheet

BACKGROUND OF THE INVENTION

My new variety of lily plant originated as a seedling which first flowered in 1985 in Boring, Ore. The breeding efforts had as their objective the production of colored, fragrant hybrids between *Lilium longiflorum* (the Easter lily) and Asiatic lilies, suited to forcing into flower out of season, heretofore unknown in the lily breeding art.

I achieved the desired objective by intercrossing a slightly fertile embryo-cultured seedling from (*Lilium longiflorum* 'Ace' (unpatented)×'Sterling Star' (unpatented)) with 'Red Carpet' (unpatented). The seed parent was the diploid form of the Dutch cultivar 'Longistar' (unpatented), which had limited commercial distribution in the Netherlands and the United States. This cultivar does not normally produce fertile seed; it can be used in breeding only if its embryos are artificially cultured. The pollen parent, the Canadian hybrid 'Red Carpet', was commercially available in the United States as a garden lily and pot-plant cultivar during the 1970's, but it was not widely grown. The embryo that produced 'Coral Fashion' was artificially cultured.

The flowers of my new lily are characterized by an very large, fragrant, deep coral upfacing to outfacing flowers with an "open bell" form with slightly clawed tepals, quite narrow at the base and broadest just below the midpoint of the bud and flower, and with tepal tips flattening but never truly recurving. This unique flower form is intermediate between the trumpet-form of *Lilium longiflorum* and the "flat-faced" Asiatic hybrid form with recurved tepal tips. The new clone possesses unusually strong, stout, almost woody stems. In addition, the clone possesses to a high degree desirable characteristics of hybrid vigor. The clone is a good grower and propagator, as observed at Boring, Ore.

My new variety of lily plant has been asexually reproduced by me and under my direction at Boring, Oreg. Successive generations produced by natural propagation from bulblets, by bulb scale propagation, and by tissue culturing from bulb scale explants have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing, which shows the open bloom in full color and illustrates the flower form, the tepal arrangement, and in particular the novel and distinctive deep coral coloration and "open bell" flower and bud form (with tepals quite narrow at the apex and broadest just below the midpoint of the bud or tepal, with tepal tips opening wide and flattening but not truly recurving at the tips).

DESCRIPTION OF THE NEW VARIETY

The following is a detailed description of my new variety of Longiflorum hybrid lily, with nomenclature according to the *International Lily Register* (Royal Horticultural Society of London, Second Edition, 1969), and with color designations according to The Colour Chart of The Royal Horticultural Society, published by the Society in 1966.

The Plant

Origin: Embryo-cultured seedling.

Seed parent: (*Lilium longiflorum* 'Ace'×'Sterling Star').

Pollen parent: 'Red Carpet'.

Commercial classification: Hybrid Lilium clone.

Horticultural classification: This clone best fits Division V, Longiflorum hybrid lily, according to the Horticultural Classification of Lilies, Royal Horticultural Society of London. This clone actually links Division V with Division I (Asiatic hybrids), however, indicating that The RHS Horticultural Classification will eventually have to be revised to accomodate such hybrids.

Form: Single stem, erect and stately.

Height: 1 to 2 m from bulbs 14 to 20 cm in circumference, provided their light levels are adequate; low light levels may cause "stretching."

Growth: Vigorous and upright.

Foliage quantity: Abundant.

Size of leaf: 10 to 15 cm long, 2 to 4 cm wide.

Shape of leaf: Lanceolate (pointed).

Texture: Leathery and glossy.

Color: Medium to dark green, lighter on lower side.

Bulb size: Any size, ranging to 25 cm circumference commercially.

Bulb color: White, with flushes of pink or yellow after exposure to light.

The Bud

Form: Obtuse, ovoid, and long.

Size: 10 to 14 cm long and 10 to 14 cm in circumference just prior to opening.

Opening: Bud opens slowly, in response to morning light; this takes about one hour.

Color: RHS CC red 53 C/D, with green tips just prior to opening. Color is very sensitive to heat and light levels and may bleach to RHS CC greyed red 180 B/C under adverse light and heat growing conditions.

Peduncle: Averages 10 to 16 cm, but it may elongate if light levels are too low, if bulbs have been improperly stored prior to forcing, or if bulbs are very large, producing an unusually large inflorescence. Color is deep plum over green, appearing almost black to the eye.

The Flower

Blooming habit: Annually in midseason; flowers once and profusely.

Size: Flowers are very large-sized, averaging 15 to 20 cm in diameter, flattening at the tips on the second day to 15 to 18 cm in diameter. The tepals are broad: outer tepals are 3 to 4 cm wide, and the inner tepals are 5 to 8 cm wide.

Borne: In a single racemic inflorescence producing 8 to 20 flowers from a bulb 14 to 16 cm in circumference. Large bulbs produce an inflorescence with many secondary and even tertiary buds. In the larger inflorescences, the flowers are more outfacing and less upfacing.

Shape: Form a broad "open bell" shape by the second day after opening, quite narrow at the base and with the broadest part of the tepals just below their midpoint. The tepal tips flatter but do not recurve.

Tepalage: Typical of genus Lilium, with 6 imbricated tepals.

Tepal color: RHS CC red 47 B/C, deepening to 53 B/C at the center of each tepal just above the nectaries. The color is actually a blend of apricot carotenes and deep magenta rose anthocyanins, and the latter are strongly affected by growing temperatures and light levels. If growing conditions of great heat or low light decrease or destroy anthocyanin production, the color apparent to the eye may shade into lighter and more orange tones, ranging to RHS greyed red 180 A/B. The anthocyanin pigment remains deepest just above the nectaries and along the tepal margins in any case.

Tepal spotting: The basal one-third of the tepals is lightly spotted with medium magenta spots, in the area parallel to the nectaries.

Tepal longevity: Tepals stay on stems about three weeks.

Pedicel length: Average 8 to 12 cm long.

Pedicel color: Dark green with deep plum overlay; appear almost black to the eye.

Pedical form: Sturdy and ascending. Large inflorescences may carry many secondary and tertiary buds, in which case many of the pedicels become more horizontal.

Color changes: Flowers become more coral-rose and less orange, but slightly lighter, as the flowers age. Low light levels and extreme heat may cause them to become much lighter.

Appearance: Flower is shiny.

Disease resistance: The flower and plant are resistant to disease; in particular, they are resistant to Fusarium bulb rot and Botrytis blight.

Fragrance: Fragrance similar to that of *Lilium longiflorum*, but lighter.

Lasting quality: The flower is long lasting, both on the plant and as a cut-flower.

The Reproductive Organs

Stamens: Arrangement typical of genus Lilium. Six stamens with RHS CC greyed red 182 D filaments 7 to 9 cm long.

Pollen and anthers (dehisced): RHS CC greyed orange 175 A/B to greyed purple 183 A.

Pistil: One in number, very soft plum, 7 to 9 cm long.

Stigma: Soft apricot (RHS CC orange red 33 D) to white, large in size.

Characteristics of ovary: Characteristics of genus Lilium.

The Fruit

Fertility: The fruit bears a few fertile seed, but most embryos require embryo culturing.

Shape: Ovoid.

Color at maturity: Soft brown, overlaid with soft plum.

My new variety of *Lilium longiflorum*/Asiatic hybrid lily most nearly resembles 'Longistar' in flower form, but it has a deeper "bell" form and broader tepals. It is deep coral red in color rather than cream-white, and it has black stems and more fragrant flowers. It also resembles its embryo-cultured sibling 'Red Ace' (unregistered name); 'Red Ace' is completely outfacing, has very long vertical pedicels on its secondary buds, and has orange-red flowers (RHS CC 32 A to 41 B) flowers that fade rapidly in bright light.

I claim:

1. A new and distinctive variety of *Lilium longiflorum*/Asiatic hybrid lily plant substantially as herein shown and described, characterized by its high resistance to disease; its tolerance of virus; its vigorous growth and rapid natural propagation; the excellence of its flower form, size, and substance, its versatility both as a garden plant and as a cut-flower/pot plant produced from pre-cooled bulbs forced under glass out of season; and in particular by its unique fragrant coral red "open bell" flowers, a combination unique among hybrid lilies suited to forcing and to mass commercial cultivation.

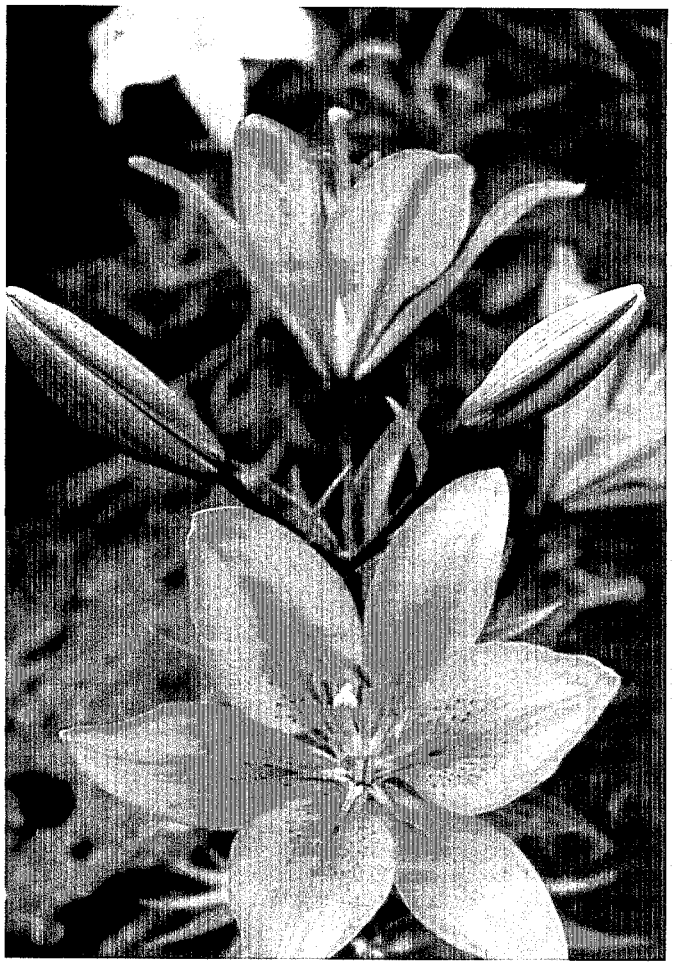

* * * * *